(12) United States Patent
McCloskey et al.

(10) Patent No.: US 9,364,372 B2
(45) Date of Patent: Jun. 14, 2016

(54) SAFETY GLASSES VERIFICATION

(71) Applicant: Honeywell International Inc., Morristown, NJ (US)

(72) Inventors: Scott McCloskey, Minneapolis, MN (US); Ryan A. Lloyd, Apple Valley, MN (US)

(73) Assignee: Honeywell International Inc., Morris Plains, NJ (US)

( * ) Notice: Subject to any disclaimer, the term of this patent is extended or adjusted under 35 U.S.C. 154(b) by 485 days.

(21) Appl. No.: 13/686,540

(22) Filed: Nov. 27, 2012

(65) Prior Publication Data
US 2013/0147938 A1  Jun. 13, 2013

Related U.S. Application Data

(60) Provisional application No. 61/564,606, filed on Nov. 29, 2011.

(51) Int. Cl.
| | |
|---|---|
| *G06Q 10/10* | (2012.01) |
| *G06Q 30/02* | (2012.01) |
| *G06Q 30/06* | (2012.01) |
| *G06Q 10/04* | (2012.01) |
| *G06Q 10/06* | (2012.01) |
| *A61F 9/02* | (2006.01) |
| *G06Q 30/00* | (2012.01) |
| *G06K 9/20* | (2006.01) |

(52) U.S. Cl.
CPC . *A61F 9/029* (2013.01); *A61F 9/02* (2013.01); *G06K 9/2018* (2013.01); *G06Q 30/018* (2013.01)

(58) Field of Classification Search
CPC .................................................. G06Q 30/018
USPC ................................................. 705/1.1–912
See application file for complete search history.

(56) References Cited

U.S. PATENT DOCUMENTS

| | | | | |
|---|---|---|---|---|
| 4,855,186 | A * | 8/1989 | Grolig et al. ................... | 428/216 |
| 2004/0145802 | A1 * | 7/2004 | Miniutti et al. ................ | 359/356 |
| 2007/0291231 | A1 * | 12/2007 | Hammoud et al. ........... | 351/222 |
| 2009/0161918 | A1 | 6/2009 | Heller et al. | |
| 2011/0007950 | A1 * | 1/2011 | Deutsch ......................... | 382/111 |
| 2011/0010023 | A1 * | 1/2011 | Kunzig et al. ..................... | 701/2 |
| 2012/0146789 | A1 * | 6/2012 | De Luca et al. ................ | 340/540 |

FOREIGN PATENT DOCUMENTS

WO   2011/123741   10/2011

OTHER PUBLICATIONS

EP Search Report related to EP Application 12194707.1, dated Jun. 13, 2014 (4 pages).

(Continued)

*Primary Examiner* — Jonathan Ouellette
(74) *Attorney, Agent, or Firm* — Brooks, Cameron & Huebsch, PLLC

(57) ABSTRACT

Safety glasses verification methods and devices are described herein. One method in accordance with the present disclosure includes capturing an RGB image of an individual, capturing an infrared (IR) image of the individual, and verifying safety glasses are being worn by the individual based on the RGB image and the IR image.

18 Claims, 3 Drawing Sheets

(56) References Cited

OTHER PUBLICATIONS

Yuki Nota, et al. "Augmenting Real-world Objects by Detecting, Invisible Visual Markers", Symposium on User Interface Software Technology, Oct. 1, 2008, pp. 39-40.

Hanhoon Park, et al. "Invisible marker based augmented reality system", Proceedings of SPIE, vol. 5960, Jul. 1, 2005, pp. 596011-596011-8.

* cited by examiner

SAFETY GLASSES VERIFICATION

CROSS-REFERENCE TO RELATED APPLICATIONS

This application is a non-provisional of U.S. Provisional Application Ser. No. 61/564,606, filed Nov. 29, 2011, the entire specification of which is incorporated herein by reference.

TECHNICAL FIELD

The present disclosure relates to methods and devices for safety glasses verification.

BACKGROUND

Despite the availability and effectiveness of personal protective equipment (PPE) (e.g., safety glasses such as goggles), the US Centers for Disease Control and Prevention report that each day more than 100 eye injuries occur on the job. On the job injuries can result in lost time at work, significant financial losses to employers, employees, and/or society through long-term disability, and/or human suffering. Some of these losses from on the job eye injuries can be prevented by proper use of PPE such as safety goggles.

Mandated compliance with workplace safety rules may not be enforced effectively. For example, in general a supervisor physically walks around a manufacturing floor to verify an employee has the proper PPE. This approach can be time intensive and inaccurate, as it does not verify correct PPE usage.

DETAILED DESCRIPTION

Figure 1:
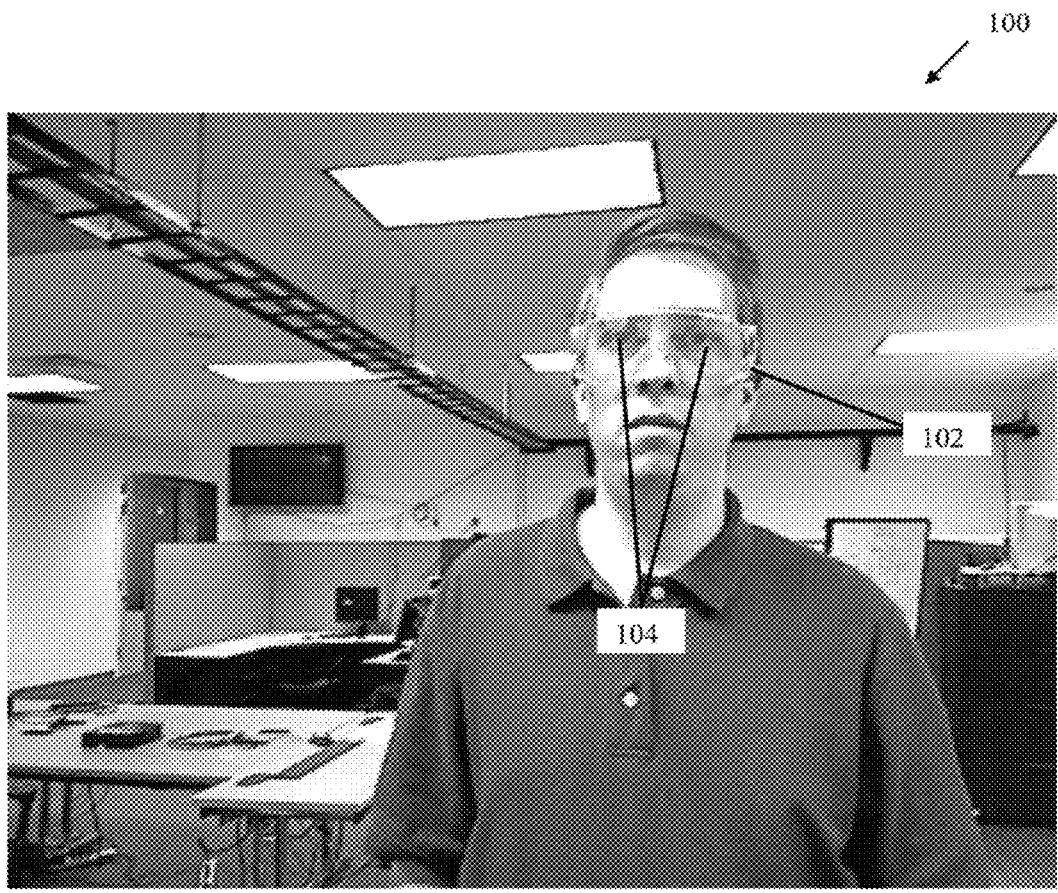
FIG. 1 illustrates an RGB image for safety glasses verification in accordance with one or more embodiments of the present disclosure.

Safety glasses verification methods and devices are described herein. For example, one or more embodiments include capturing an RGB image of an individual, capturing an infrared (IR) image of the individual, and verifying safety glasses are being worn by the individual based on the RGB image and the IR image.

Safety glasses do not provide a benefit (e.g., decrease the risk of eye injuries) unless they are utilized in a designated manner (e.g., worn properly on the face of an individual such that the individual's eyes are covered). Therefore, merely verifying that safety glasses are present (e.g., in an individual's possession) may not be enough to decrease the occurrence of eye injuries. Rather, verifying that safety glasses are present and are properly worn (e.g., covering the eyes of an individual) may effectively decrease the occurrence of eye injuries.

In some embodiments, a multi-band image approach for safety glasses verification can be used. A multi-band image can include images with multiple wavelength exposures that have been combined, blended, layered, and/or combinations thereof. For example, an RGB (e.g., visual) image can be combined with an infrared (IR) image in order to achieve aspects of the visible wavelength spectrum (e.g., 390 to 750 nanometers (nm)) and/or the IR wavelength spectrum (e.g., 0.78 to 1000 micrometers ($\mu m$)).

The IR wavelength spectrum can include, for example: near-infrared (NIR) in a range of from 0.75 $\mu m$ to 1.4 $\mu m$; short-wavelength infrared (SWIR) in a range of from 1.4 $\mu m$ to 3 $\mu m$; mid-wavelength infrared (MWIR) in a range of from 3 $\mu m$ to 8 $\mu m$: long-wavelength infrared (LWIR) in a range of from 8 $\mu m$ to 15 $\mu m$; and/or far infrared (FIR) at 15 $\mu m$ to 1000 $\mu m$.

The embodiments of the present disclosure can reduce manpower spent in manual safety glasses verification, reduce error in a manual safety glasses inspection process, decrease eye injuries, reduce costs associated with eye injuries, and/or combinations thereof, among other benefits. This can be accomplished, for example, by automating safety glasses verification using multi-band imaging.

The figures herein follow a numbering convention in which the first digit corresponds to the drawing figure number and the remaining digits identify an element or component in the drawing. Similar elements or components between different figures can be identified by the use of similar digits. For example, 104 can reference element "04" in FIG. 1, and a similar element can be referenced as 204 in FIG. 2.

FIG. 1 illustrates an RGB image 100 for safety glasses verification in accordance with one or more embodiments of the present disclosure. An RGB (e.g., visual) image can include images that have combinations of up to three channels (e.g., colors) within the visual (e.g., visible) spectrum: red, green, and blue (e.g., an RGB image can include light from the visible spectrum). RGB image 100 can be based on ambient illumination and captured by a camera, as will be further described herein (e.g., in connection with FIG. 3)

As shown in FIG. 1, the RGB image 100 includes a pair of safety glasses 102 being worn by an individual. The safety glasses 102 can be any type of glasses (e.g., goggles) used in industry for eye protection.

In some embodiments, eye or eyes 104 of the individual can be detected (e.g., located) in the RGB image 100. The eye(s) can be detected by, for example, biometric detection software (e.g., the eyes can be biometrically detected). For example, an eye detection routine may be employed from a publicly available library, such as, for example, Open Source Computer Vision (OpenCV).

In some embodiments, the head position of the individual in the image 100 can be detected, Such embodiments may not directly detect the eyes of the user. For example, after detecting the head of the individual, pose estimation techniques can be used to infer the location of the eyes of the individual based on the positioning of the individual's head. Such embodiments can, for example, provide the benefit of increased robustness to distortions imposed by the safety glasses, in some implementations.

Figure 2:
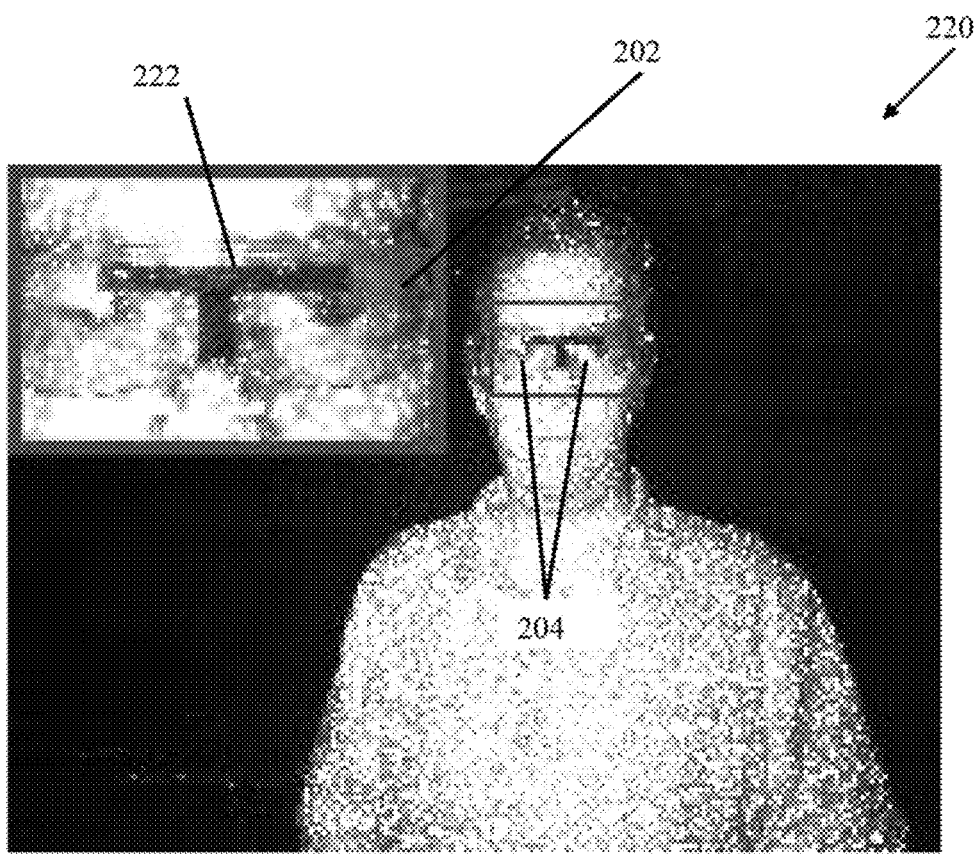
FIG. 2 illustrates an infrared (IR) image for safety glasses verification in accordance with one or more embodiments of the present disclosure.

FIG. 2 illustrates an infrared (IR) image 220 for safety glasses verification in accordance with one or more embodiments of the present disclosure. An IR image can include light from the IR spectrum and can be taken using film and/or an image sensor sensitive to IR light.

As shown in FIG. 2, IR image 220 can be the corresponding IR image of the RGB image 100 (e.g., IR image 220 can be IR image of the subject captured in RGB image 100). IR image 220 can be captured from an active IR (e.g., NIR) illumination source by a camera, as will be further described herein (e.g. in connection with FIG. 3).

Safety glasses 202 corresponding to detected eye location(s) 204 can be detected (e.g., verified) in IR image 220. That is, the location of safety glasses 202 can be detected in IR image 220, and it can be verified that the location of safety glasses 202 corresponds to the detected eye location(s) 204.

For example, previous safety glasses may include plastic which is clear (e.g., not visible) in the visible spectrum and/or the IR spectrum. In contrast, safety glasses in accordance with the present disclosure (e.g., safety glasses 202) can include a material that is not visible in RGB images (e.g., a material that is visibly clear), but is visible in IR images. For instance, a material used to form a portion of the frame and/or lenses of the glasses may have such properties, and/or or may be impregnated and/or coated with a substance (e.g., dye) having such properties (e.g., an IR absorbing substance).

For example, in the embodiment illustrated in FIG. 2, a piece of film 222 impregnated with an IR-absorbing substance (e.g., dye) can be included in and/or on the safety glasses 202. For instance, the film 222 can be placed on the frame of the safety glasses, on the lenses of the safety glasses, and/or combinations thereof.

As shown in FIG. 2, film 222 can be in the shape of a "T" corresponding to a center of the frame of safety glasses 202. Such a "T" shape can enable the individual's eye to be located on either side of the vertical section of the "T" to indicate that the glasses are being worn and are properly positioned. However, embodiments of the present disclosure are not limited to such a "T" shape, and any other suitable shape for film 222 can be utilized in various embodiments of the disclosure.

IR-absorbing substances can include, for example, substances that absorb IR wavelengths causing the substance to be visible in IR images (e.g., as a dark shape on a bright background). Some embodiments can include IR-absorbing substances visible in one or more of the IR wavelength ranges discussed herein. For example, the IR-absorbing substance can be a NIR absorbing substance. However, embodiments of the present disclosure are not limited to a particular type of IR absorbing substance.

Figure 3:
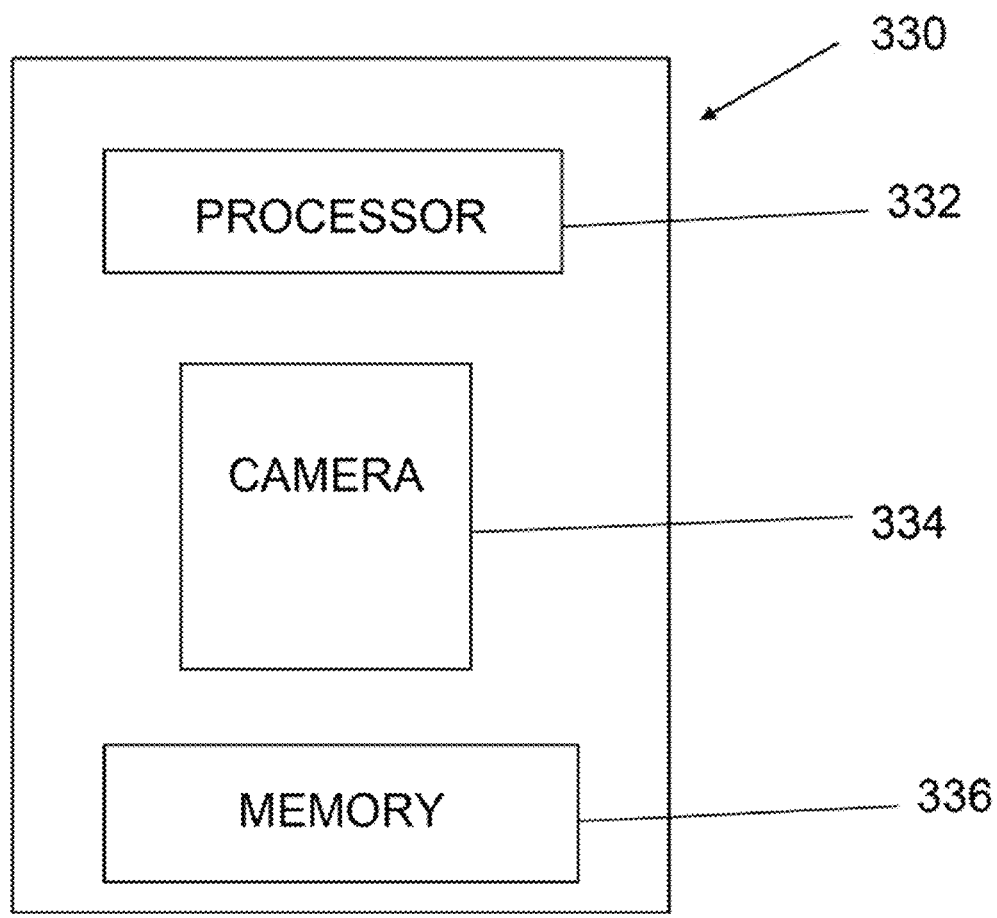
FIG. 3 illustrates a safety glasses verification device in accordance with one or more embodiments of the present disclosure.

FIG. 3 illustrates a safety glasses verification device 330 in accordance with one or more embodiments of the present disclosure. As shown in FIG. 3, verification device 330 can include a camera 334. Camera 334 can include, for example, a camera capable of capturing RGB images (e.g., RGB image 100 previously described in connection with FIG. 1), IR images (e.g., IR image 220 previously described in connection with FIG. 2), and/or combinations thereof. That is, camera 334 can be a dual-band camera with an IR illumination (e.g., light) source.

Some embodiments can include a single verification device (e.g., verification device 330) that captures both the RGB and IR images simultaneously via (e.g., using) camera 334. Such embodiments can provide lower equipment costs, among other benefits. Some embodiments can include separate verification devices capable of capturing an RGB image and IR image approximately simultaneously via (e.g., using) multiple cameras (e.g., a first verification device can capture the RGB image via a first camera, and a second verification device can capture the IR image via a second camera). Such embodiments can reduce the engineering of a multi-camera system, among other benefits.

As shown in FIG. 3, verification device 330 can include a processor 332 and a memory 336 coupled to the processor 332. Memory 336 can be volatile or nonvolatile memory. Memory 336 can also be removable (e.g., portable) memory, or non-removable (e.g., internal) memory. For example, memory 336 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disk, a digital versatile disc (DVD) or other optical disk storage, and/or a magnetic medium such as magnetic cassettes, tapes, or disks, among other types of memory.

Further, although memory 336 is illustrated as being located in verification device 330, embodiments of the present disclosure are not so limited. For example, memory 336 can also be located internal to another computing resource (e.g., enabling computer readable instructions to be downloaded over the Internet or another wired or wireless connection).

Memory 336 can be any type of storage medium that can be accessed by processor 332 to perform various examples of the present disclosure. For example, memory 336 can be a non-transitory computer readable medium having computer readable instructions (e.g., computer program instructions) stored thereon that are executable by processor 332 to capture RGB images and/or IR images, register images, perform biometric detection and/or IR-absorbing substance (e.g., dye) detection, and/or combinations thereof, in accordance with one or more embodiments of the present disclosure. That is, processor 332 can execute the executable instructions stored in memory 336 to capture RGB images and/or IR images, register images, perform biometric detection and/or IR-absorbing substance (e.g., dye) detection, and/or combinations thereof, in accordance with one or more embodiments of the present disclosure. Memory 336 can also store the captured images and/or data associated therewith.

Some embodiments can include registering the RGB image and the IR image. Registering can include matching the images according to reference points common to each image. For example, reference points may be inserted in a corner(s) of each image and imaging software may correlate each reference point of the RGB image to the IR image to aid in registering the images. The registering can ensure that the location of the eyes and the location of the detected glasses overlap. This can be accomplished, in some embodiments, by inserting reference point data into a data set of image data.

Some embodiments of the present disclosure can use multi-band (e.g., RGB and IR) imaging to verify safety glasses. Safety glasses verification can include detecting one or more of an individual's eye locations and detecting the presence of safety glasses in proximity to the individual's eye locations and/or orientation of the glasses with respect to one or more of the individual's eyes. This can verify that the safety glasses are present and worn properly, among other benefits.

If detected (e.g., located) eyes in the RGB image have no corresponding safety glasses detection (e.g., location) in the IR image, a safety policy violation, for example, can be flagged. In some embodiments, the images can be stored in memory (e.g., memory 336) and/or transmitted for further processing, such as manual verification.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of devices" can refer to one or more devices.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method for verifying safety glasses, comprising:
   capturing an RGB image of an individual;
   capturing an infrared (IR) image of the individual; and
   verifying, by a safety glasses verification device, safety glasses are being properly worn by the individual based on the RGB image and the IR image by:
     detecting a location of an eye of the individual in the RGB image;
     detecting a location of safety glasses in the IR image, wherein:
       the safety glasses include a single T-shaped material corresponding exclusively to a center of a frame of the safety glasses; and
       the single T-shaped material is visible in the IR image and not visible in the RGB image; and
     verifying that the location of the eye of the individual in the RGB image corresponds to the location of the safety glasses in the IR image.

2. The method of claim 1, wherein detecting the location of the eye of the individual in the RGB image includes:
   detecting a position of the individual's head in the RGB image; and
   inferring the location of the eye of the individual in the RGB image based on the position of the individual's head in the RGB image.

3. The method of claim 1, wherein verifying safety glasses are being properly worn by the individual includes verifying that the safety glasses are covering both eyes of the individual.

4. The method of claim 1, wherein the method includes capturing the RGB image and the IR image using a single camera.

5. The method of claim 1, wherein the method includes:
   capturing the RGB image using a first camera; and
   capturing the IR image using a second camera.

6. The method of claim 1, wherein the IR image of the individual is a corresponding IR image of the RGB image of the individual.

7. The method of claim 1, wherein the method includes capturing the RGB image and the IR image simultaneously.

8. A safety glasses verification device, comprising:
   a camera configured to capture an RGB image of an individual and an infrared (IR) image of the individual;
   a memory; and
   a processor configured to execute executable instructions stored in the memory to:
     detect a location of an eye of the individual in the RGB image;
     detect a location of safety glasses in the IR image, wherein:
       the safety glasses include a single T-shaped material corresponding exclusively to a center of a frame of the safety glasses; and
       the single T-shaped material is visible in the IR image and not visible in the RGB image; and
     verify that the location of the eye of the individual in the RGB image corresponds to the location of the safety glasses in the IR image to verify that the safety glasses are being properly worn by the individual.

9. The safety glasses verification device of claim 8, wherein the processor is configured to execute the instructions to verify that the location of the eye of the individual in the RGB image corresponds to the location of the safety glasses in the IR image by registering the RGB image and the IR image.

10. The safety glasses verification device of claim 9, wherein registering the RGB image and the IR image includes matching the RGB image and the IR image according to reference points common to each image.

11. The safety glasses verification device of claim 8, wherein the memory is configured to store the RGB image and the IR image.

12. The safety glasses verification device of claim 8, wherein the processor is configured to execute the instructions to flag a safety violation if the location of the eye of the individual in the RGB image does not correspond to the location of the safety glasses in the IR image.

13. The safety glasses verification device of claim 8, wherein the processor is configured to execute the instructions to biometrically detect the location of the eye of the individual in the RGB image.

14. A safety glasses verification device, comprising:
   a camera configured to capture an RGB image of an individual and an infrared (IR) image of the individual;
   a memory; and
   a processor configured to execute executable instructions stored in the memory to verify safety glasses are being properly worn by the individual based on the RGB image and the IR image by:
     detecting a location of an eye of the individual in the RGB image;
     detecting a location of safety glasses in the IR image, wherein the safety glasses include a material that is:
       a single T-shaped material corresponding exclusively to a center of a frame of the safety glasses;
       visible in the IR image; and
       not visible in the RGB image; and
     verifying that the location of the eye of the individual in the RGB image corresponds to the location of the safety glasses in the IR image.

15. The safety glasses verification device of claim 14, wherein the material includes an IR-absorbing substance.

16. The safety glasses verification device of claim 14, wherein the material is a film impregnated with an IR-absorbing substance.

17. The safety glasses verification device of claim 14, wherein the material forms a portion of the center of the frame of the safety glasses.

18. The safety glasses verification device of claim 14, wherein the material is placed on the center of the frame of the safety glasses.

* * * * *